(12) United States Patent
Murray

(10) Patent No.: US 11,766,162 B2
(45) Date of Patent: Sep. 26, 2023

(54) DISPOSABLE ENDOSCOPE COVER, REUSABLE ENDOSCOPE, AND SYSTEM

(71) Applicant: BEAVER-VISITEC INTERNATIONAL, INC., Waltham, MA (US)

(72) Inventor: Collin Murray, Maynard, MA (US)

(73) Assignee: BEAVER-VISITEC INTERNATIONAL, INC., Waltham, MA (US)

( * ) Notice: Subject to any disclaimer, the term of this patent is extended or adjusted under 35 U.S.C. 154(b) by 449 days.

(21) Appl. No.: 16/153,183

(22) Filed: Oct. 5, 2018

(65) Prior Publication Data

US 2019/0104928 A1    Apr. 11, 2019

Related U.S. Application Data

(60) Provisional application No. 62/569,107, filed on Oct. 6, 2017.

(51) Int. Cl.
*A61B 1/00* (2006.01)
*A61B 1/07* (2006.01)
*A61B 18/24* (2006.01)

(52) U.S. Cl.
CPC ........ *A61B 1/00103* (2013.01); *A61B 1/0014* (2013.01); *A61B 1/00096* (2013.01); *A61B 1/00142* (2013.01); *A61B 1/07* (2013.01); *A61B 18/24* (2013.01)

(58) Field of Classification Search
CPC ............ A61B 1/00103; A61B 1/00142; A61B 1/00096; A61B 1/0014; A61B 1/07; A61B 18/24; A61B 1/00135

USPC .................................................. 600/125, 263
See application file for complete search history.

(56) References Cited

U.S. PATENT DOCUMENTS

| | | | | |
|---|---|---|---|---|
| 4,986,262 A | * | 1/1991 | Saito | ........................ A61B 1/05 600/108 |
| 5,168,863 A | * | 12/1992 | Kurtzer | .............. A61B 1/00142 206/363 |
| 5,257,617 A | * | 11/1993 | Takahashi | .......... A61B 1/00142 600/123 |

(Continued)

FOREIGN PATENT DOCUMENTS

JP    H05208022 A  *  8/1993

OTHER PUBLICATIONS

International Search Report and Written Opinion from PCT Appl. No. PCT/US2018/54639 dated Dec. 31, 2018.

*Primary Examiner* — Anh Tuan T Nguyen
*Assistant Examiner* — Rynae E Boler
(74) *Attorney, Agent, or Firm* — Budzyn IP Law, LLC

(57) ABSTRACT

Endoscope cover with cavity that accommodates a hand piece of an endoscope and a hollow cannula extending distally from the cavity that accommodates a probe of the endoscope when the hand piece is inserted into the cavity of the cover. A reusable endoscope with a hand piece and a probe is provided with a retractable shield covering at least a portion of the probe. A system includes a cover with a cavity and a hollow cannula extending distally from the cavity, a reusable endoscope with a hand piece and a probe extending distally from the hand piece, and a retractable shield covering at least a portion of the probe, where the cannula is configured to accommodate therein the probe when the hand piece is inserted into the cavity of the cover.

8 Claims, 7 Drawing Sheets

(56) References Cited

U.S. PATENT DOCUMENTS

| | | | | |
|---|---|---|---|---|
| 5,569,161 | A | * | 10/1996 | Ebling ................ A61B 1/00142 385/117 |
| 5,702,347 | A | | 12/1997 | Yabe et al. |
| 7,833,150 | B2 | * | 11/2010 | Yamamoto ......... A61B 1/00082 600/116 |
| 8,727,969 | B2 | | 5/2014 | Leiner |
| 2008/0064925 | A1 | * | 3/2008 | Gill .................... A61B 1/00167 600/109 |
| 2009/0043167 | A1 | * | 2/2009 | Leiner ................ A61B 1/00119 600/156 |
| 2010/0217080 | A1 | * | 8/2010 | Cheung ............. A61B 1/00135 600/121 |
| 2011/0282139 | A1 | * | 11/2011 | Uram .................... A61B 1/042 600/109 |
| 2013/0184527 | A1 | * | 7/2013 | Castellucci ........ A61B 1/00126 600/121 |
| 2014/0275765 | A1 | | 9/2014 | Gebhart et al. |
| 2014/0275767 | A1 | * | 9/2014 | Baust ..................... A61B 18/02 600/104 |
| 2016/0374546 | A1 | * | 12/2016 | Berbee ..................... A61B 1/05 600/109 |
| 2017/0079520 | A1 | * | 3/2017 | Huang ................... A61B 1/045 |
| 2017/0340350 | A1 | * | 11/2017 | Lieberman ......... A61B 1/00154 |

\* cited by examiner

DISPOSABLE ENDOSCOPE COVER, REUSABLE ENDOSCOPE, AND SYSTEM

CROSS-REFERENCE TO RELATED APPLICATIONS

This application claims priority to prior U.S. Provisional Patent Application No. 62/569,107, filed Oct. 6, 2017, the entire content of which is incorporated herein by reference.

This application is related to U.S. patent application Ser. No. 14/966,151 filed on Dec. 11, 2015, which is a continuation-in-part of U.S. patent application Ser. No. 13/084,789 filed on Apr. 12, 2011, and U.S. patent application Ser. No. 13/314,371 filed on Dec. 8, 2011, which is a continuation-in-part of U.S. patent application Ser. No. 12/779,214 filed on May 13, 2010, the entire disclosures of which are hereby incorporated by reference.

Other prior related applications are U.S. Pat. No. 5,121,740 issued on Jun. 16, 1992 and U.S. Pat. No. 6,997,868 issued on Feb. 14, 2006, the entire disclosures of which are incorporated herein by reference

BACKGROUND

1. Field of Disclosure

Generally, exemplary embodiments of the present disclosure relate to a medical laser video endoscope and more particularly to one in which the operating probe can be covered during a procedure so that the cover can be disposed of thereafter.

2. Background of Disclosure

In some of the previous version of a disposable endoscope as described and claimed in Applicant's prior applications noted above, one of the features included an image guide shortened to be configured only within a single use distal comprising a probe (for example, stainless cannula) and a hand piece (for example, a plastic body) with the camera sensor placed in a user's hand. The single use distal end also comprised a laser guide and an illumination guide extending through the plastic body and the stainless cannula and then to the respective inputs in a base unit. Other implementation provided a sterile sleeve that could be deployed along the length of the endoscope.

One of the disadvantages is that at least some of the functional components would be disposed of after a single use.

SUMMARY

Exemplary embodiments of the present disclosure address at least such drawbacks by providing devices and systems that allow functional components of an endoscope to be reused, and provide at least the advantages described below.

According to one aspect of the present disclosure there is provided a cover for an endoscope, the cover comprising a body with a cavity for accommodating a hand piece of an endoscope and a hollow cannula in sealed communication with the body and extending distally from the cavity. The cannula is configured to accommodate therein a probe extending distally from a body of a hand piece of an endoscope when the body of the hand piece is inserted into the cavity of the body of the cover.

According to another aspect of the present disclosure there is provided a reusable endoscope comprising a hand piece having a body, a probe extending distally from the body, and a retractable shield covering at least a portion of said probe.

According to yet another aspect of the present disclosure there is provided a system comprising: a cover including a body with a cavity and a hollow cannula in sealed communication with the body and extending distally from the cavity; and a reusable endoscope comprising including a hand piece having body, a probe extending distally from the body of the hand piece, and a retractable shield covering at least a portion of the probe. The cannula is configured to accommodate therein the probe when the body of the hand piece is inserted into the cavity of the body of the cover.

According to an exemplary implementation, the shield retracts when said cover is placed over the endoscope and a proximal end of the hollow cannula engages a distal end of the probe of the endoscope.

Optionally, in any of the preceding aspects, the body of the hand piece has a cavity and the shield retracts proximally into the cavity of the hand piece when the cover is placed over the endoscope and a proximal end of the hollow cannula engages a distal end of the probe of the endoscope.

Optionally, in any of the preceding aspects, the cover is configured to snap-fit onto the endoscope when the body of the hand piece is inserted into the cavity of the cover.

Optionally, in any of the preceding aspects, the cover has a sheath extendable proximally from the body of the cover.

Optionally, in any of the preceding aspects, the cover can include an optically clear window disposed at a distal end of the cannula.

Optionally, in any of the preceding aspects, the cannula can have an elongate body having at least one of a rigid portion, a flexible portion, a straight portion, and a curved portion.

Optionally, in any of the preceding aspects, the probe houses therein at least one of an image guide, an illumination guide, and a laser guide.

Optionally, in any of the preceding aspects, a retractable shield can be biased distally from the body of the hand piece toward a distal end of the probe to protect components of the probe.

Optionally, in any of the preceding aspects, the probe includes an image guide, an illumination guide, and a laser guide extending distally from a proximal end of the hand piece to a distal end of the probe.

BRIEF DESCRIPTION OF THE DRAWINGS

The above and other objects, advantages and salient features of the disclosure will become apparent to those skilled in the art from the following detailed description of illustrative embodiments thereof when taken in conjunction with the accompanying drawings in which.

DETAILED DESCRIPTION OF ILLUSTRATIVE EMBODIMENTS

The matters exemplified in this description are provided to assist in a comprehensive understanding of exemplary embodiments of the disclosure. Accordingly, those of ordinary skill in the art will recognize that various changes and modifications of the embodiments described herein can be made without departing from the scope and spirit of the disclosure. Also, descriptions of well-known functions and constructions are omitted for clarity and conciseness.

As would be readily appreciated by skilled artisans in the relevant art, while descriptive terms such as "guide", "fibers", "optics", "lenses", "distal", "proximal", "handle", "window", "sleeve", "top", "side" and others are used throughout this specification to facilitate understanding, it is not intended to limit any components that can be used in combinations or individually to implement various aspects of the embodiments of the present disclosure.

Figure 1:
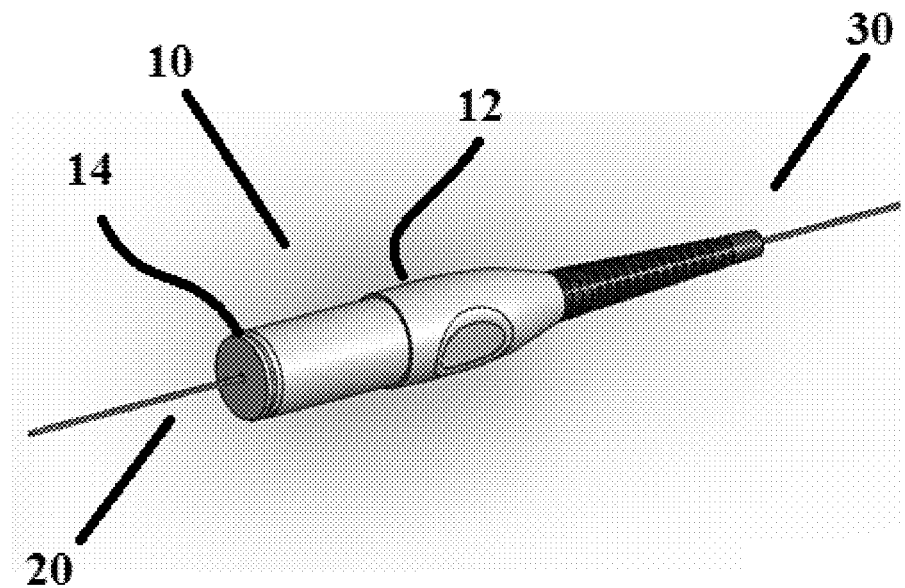
FIG. 1 illustrates an example of an endoscope according to exemplary embodiments of present disclosure.
Figure 9:
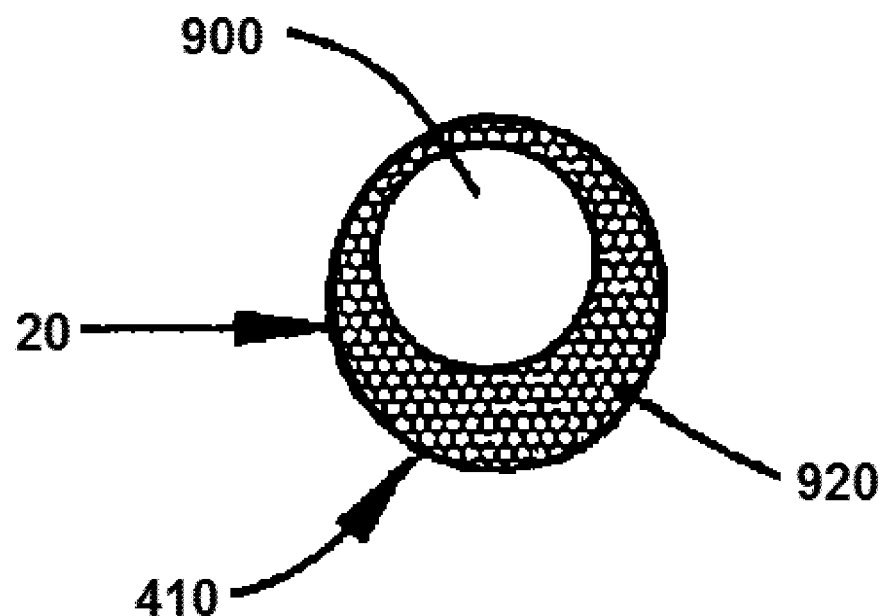
FIGS. 9 and 10 illustrate examples of cross-sectional views of probe of endoscopes according to exemplary implementations of embodiments of present disclosure.
Figure 10:
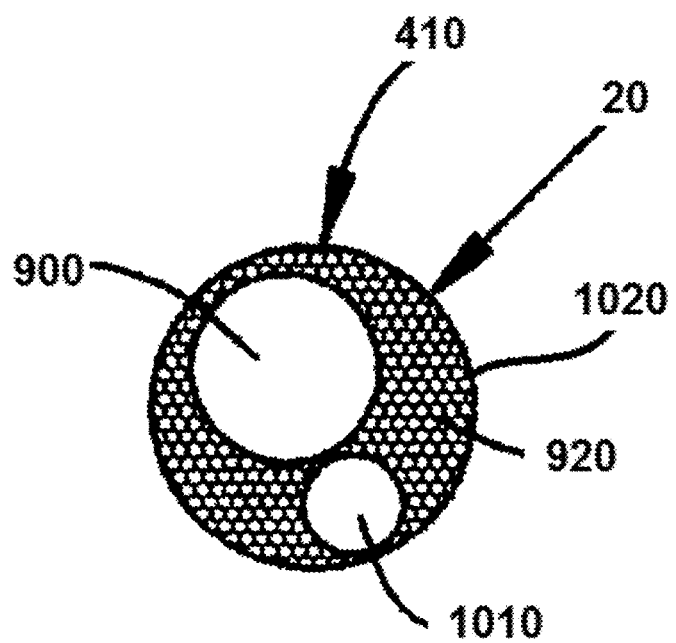

Exemplary embodiments of the present disclosure provide a disposable cover comprising a cannula with clear glass window that protects the reusable components including a hand piece 10 having a probe 20 extending distally from body 12. Referring to example of FIG. 1, and FIGS. 9 and 10 which illustrate cross sectional views of a probe 20 according to exemplary implementations, where probe 20 can optionally comprise any and all, and in any combination, imaging 900, laser 1010, and illumination 920 components 410, any and all of which can be formed of rigid and/or flexible fiber optic cable or bundle of cables, as described in the above-referenced prior patents and patent applications.

In an exemplary implementation, hand piece 10 comprises connections 30 proximally extending from body 12 to any and/or all such as imaging camera, illumination source, and/or laser source as further described in above-referenced prior patents and patent applications. In yet further exemplary implementation components of probe 20 can be housed in a flexible or rigid sheath of tube 1020.

Exemplary embodiments of the present disclosure can eliminate need for sterilization and related damage as described below.

Figure 2:
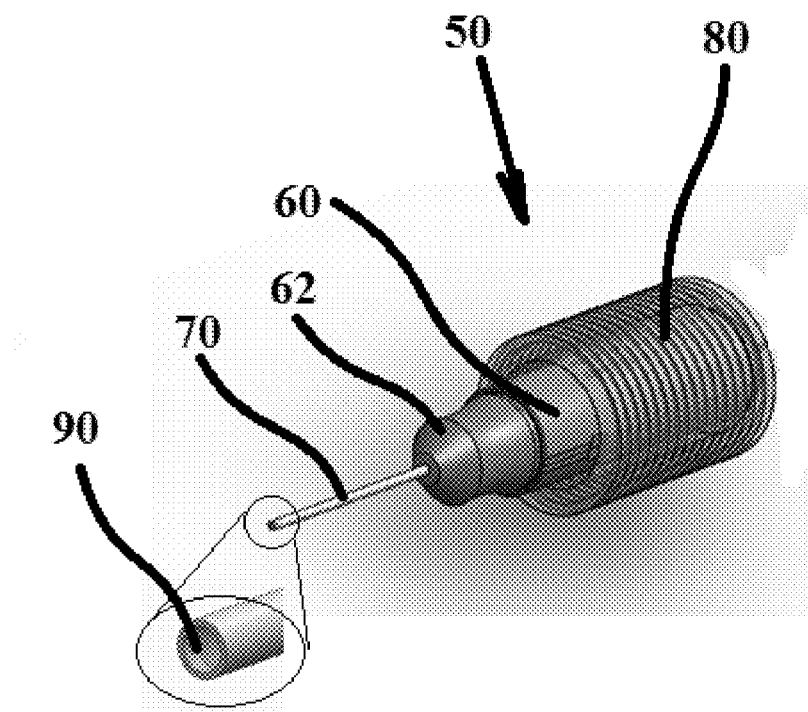
FIG. 2 illustrates an example of an endoscope cover according to exemplary embodiments of present disclosure.

Referring to an example of FIG. 2, according to exemplary implementations of the embodiments of the present disclosure, configuration of structural elements making up the disposable cover 50 include, in any combination, a reusable thin plastic extrusion 62 and handle 60 forming a cavity therein, and an optically clear window 90 inside a cannula 70 that covers existing optics of probe 20 when cover 50 is installed onto hand piece 10. Cannula 70 can be configured in sealed communication with extrusion 62 and thereby the cavity inside extrusion 62 and handle 60. In an optional exemplary implementation, a sterile cover with microbial barrier sheath 80 attached can also be included for covering of reusable portions of endoscope.

Figure 3:
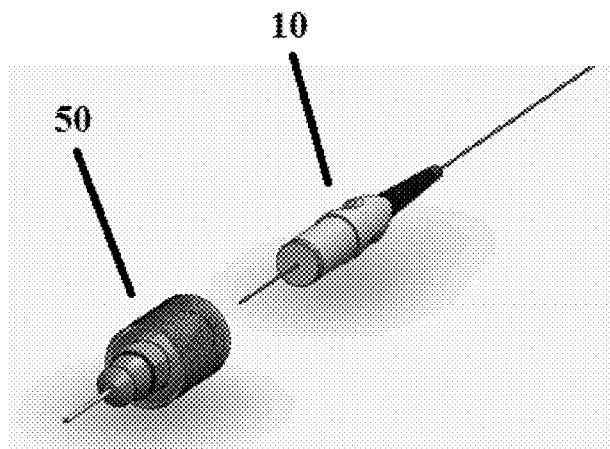
FIG. 3 illustrates an example of a system according to exemplary embodiments of the disclosure including an endoscope and an endoscope cover according to exemplary implementations of embodiments of present disclosure.

FIG. 3 illustrates an example of cover 50 with respect to hand piece 10 such that probe 20 (with or without a flexible or rigid sheath or tube covering its fiber optic components) of hand piece 10 and cannula 70 are essentially axial aligned for placement of cover 50 onto hand piece 10. In an exemplary implementation, window 90 comprises glass with index of refraction optimized to reduce visual aberrations. In yet further exemplary implementation, outer diameter, wall thickness, length, and other characteristics of cannula 70 can be optimized as described in prior applications and patents reference above.

Figure 8:
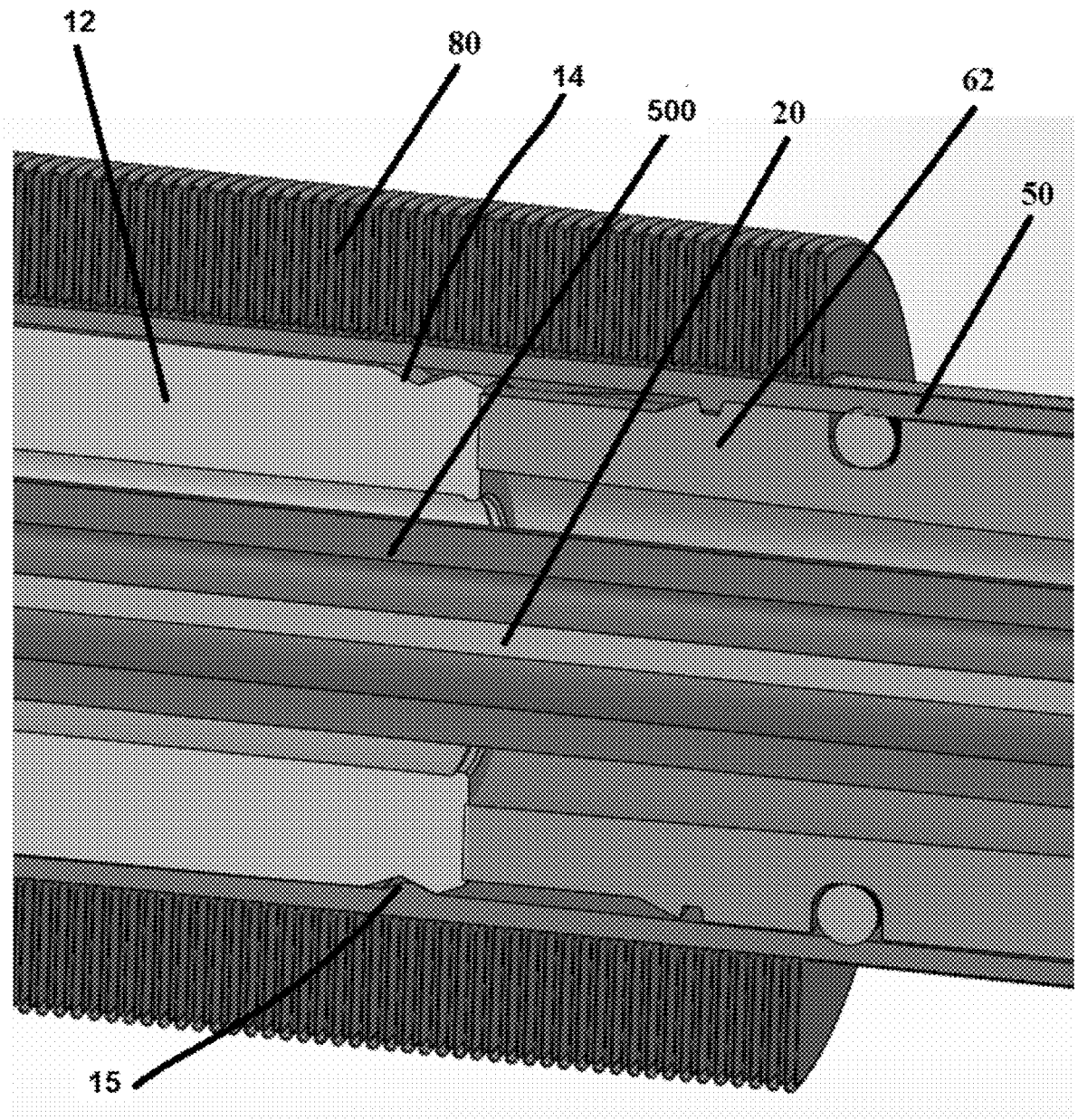
FIG. 8 diagrammatically illustrates an enlarged view of a portion of an endoscope cover engaging an endoscope according to exemplary implementations of embodiments of present disclosure.

According to still further exemplary implementations of the embodiments of the present disclosure, body 12 of hand piece 10 can include a feature 14 cooperating with a feature 15 of cover 50 to provide, for example, a snap-fit connection of cover 50 onto hand piece 10, as illustrated in the example of FIG. 8.

Figure 4:
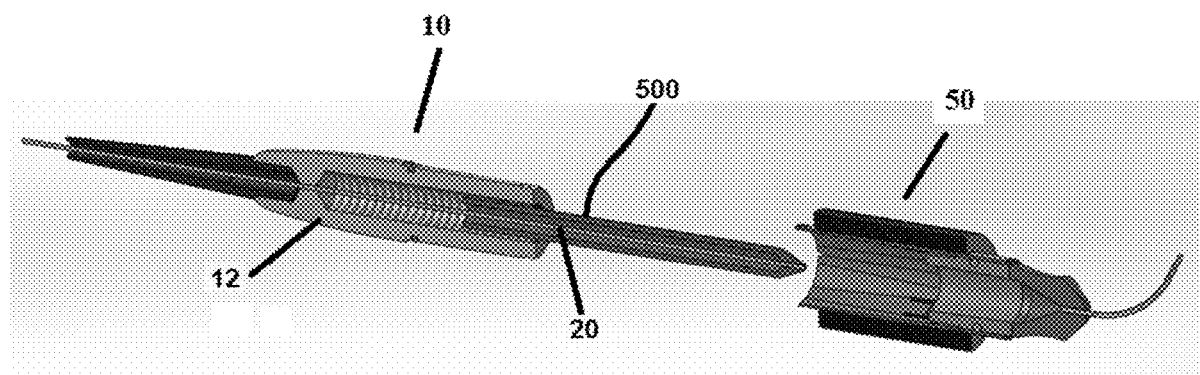
FIG. 4 illustrates another example of a system according to exemplary embodiments of the disclosure including an endoscope and an endoscope cover according to exemplary implementations of embodiments of present disclosure.
Figure 5:
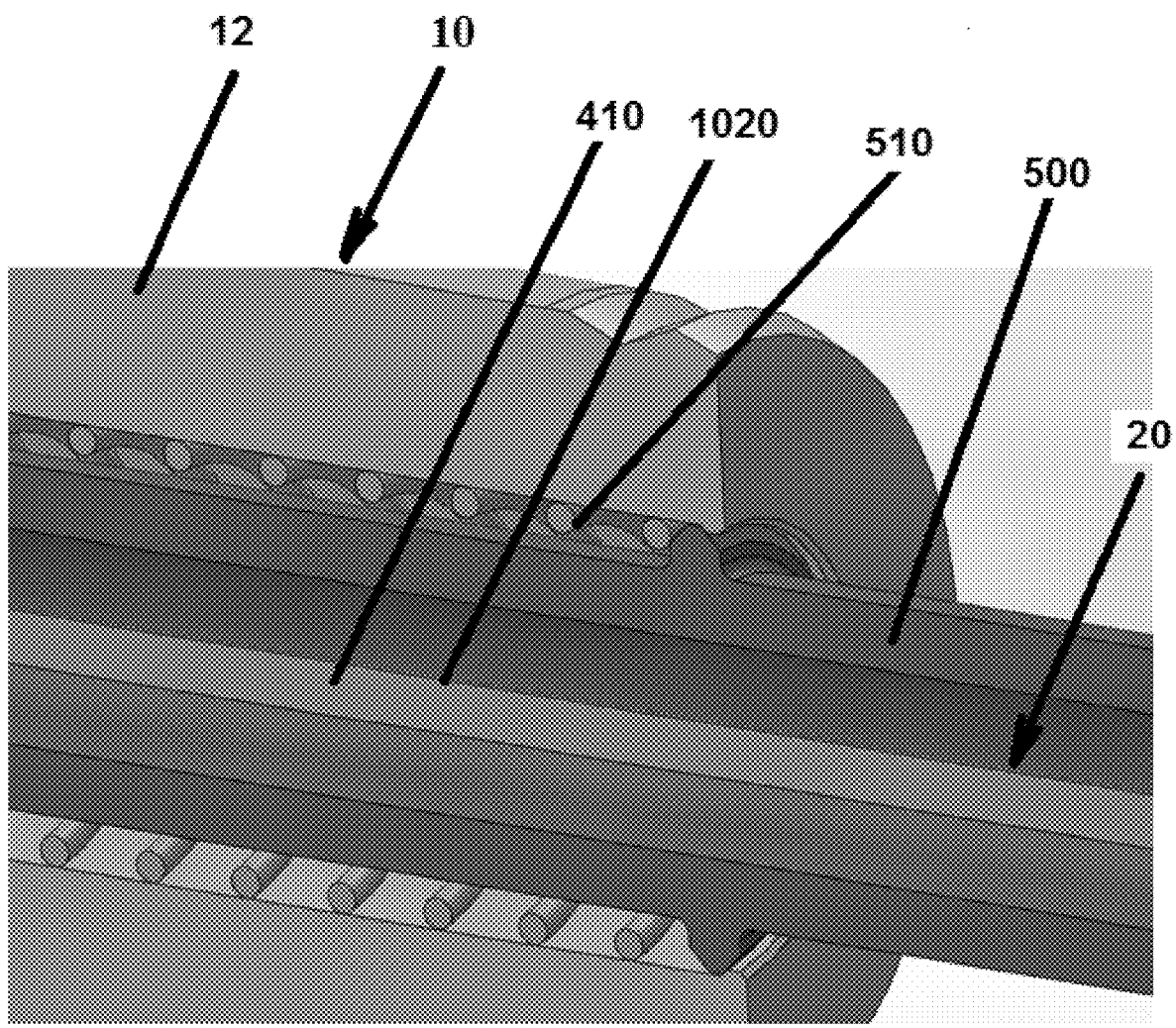
FIG. 5 diagrammatically illustrates an enlarged view of a portion of an endoscope according to exemplary implementations of embodiments of present disclosure.

Referring to FIGS. 4 and 5, according to still further exemplary implementations of the embodiments of the present disclosure, one or more of any and all various functional components 410 in any combination, including imaging, optics, laser and illumination, can reside in the reusable section including body 12 and probe 20 of hand piece 10. The component and/or components 410 can be housed in a flexible or rigid plastic extrusion 1020. In an exemplary implementation, portion of component and/or components extending distally from body of hand piece can be protected by a cover 500 that only retracts when connecting the cover with the distal end of hand piece. In an exemplary implementation, cover 500 can be spring loaded by means of a flexible element such as a spring 510.

Figure 11:
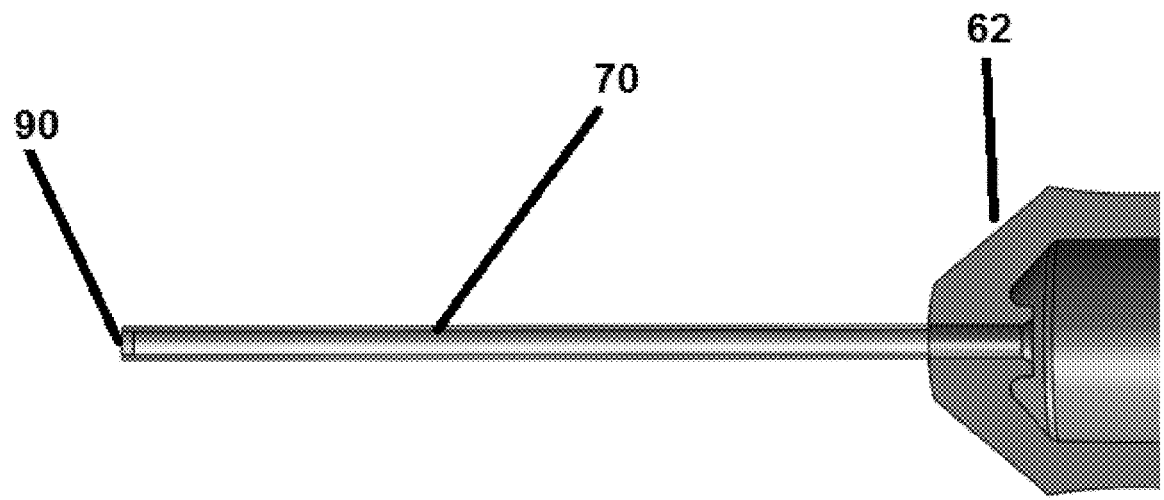
FIGS. 11 and 12 diagrammatically illustrate enlarged views of a portion of an endoscope cover according to exemplary implementations of embodiments of present disclosure.
Figure 12:
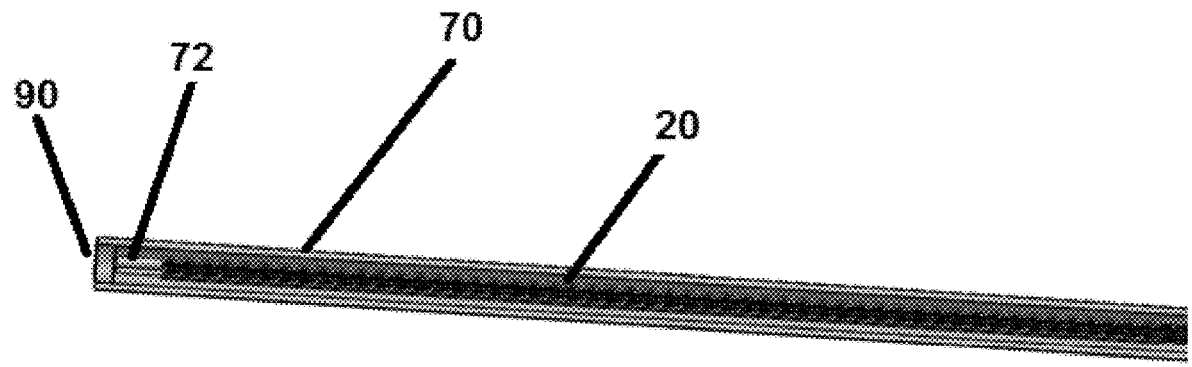

According to an exemplary implementation, as further illustrated in the example of FIGS. 11 and 12, the distal portion of hand piece 10 including probe 20 comprises any and/or all and in any combination, of components including image guide, laser guide, and/or illumination guide. Inside the protective cannula 70 of the distal end is a hollow chamber 72. The tip of the cannula is closed off by an optically clear cover 90, such as a piece of glass that can be anti-reflective coated to eliminate glare.

Figure 6:
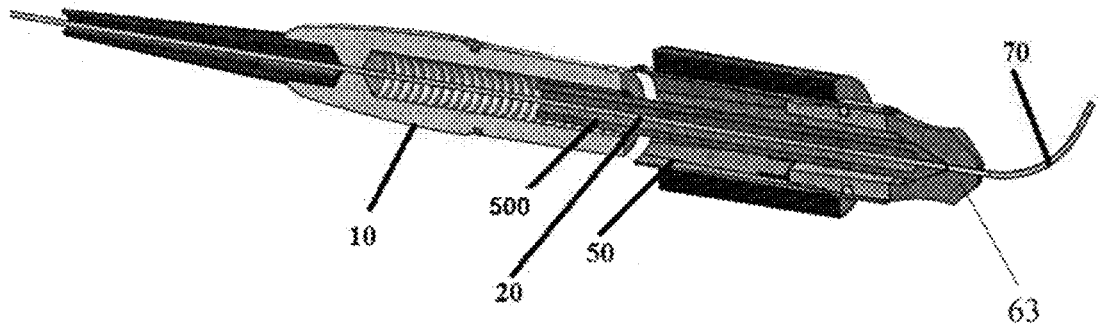
FIGS. 6 and 7 illustrate an example of different states of a system according to exemplary embodiments of the disclosure including an endoscope and an endoscope cover according to exemplary implementations of embodiments of present disclosure.
Figure 7:
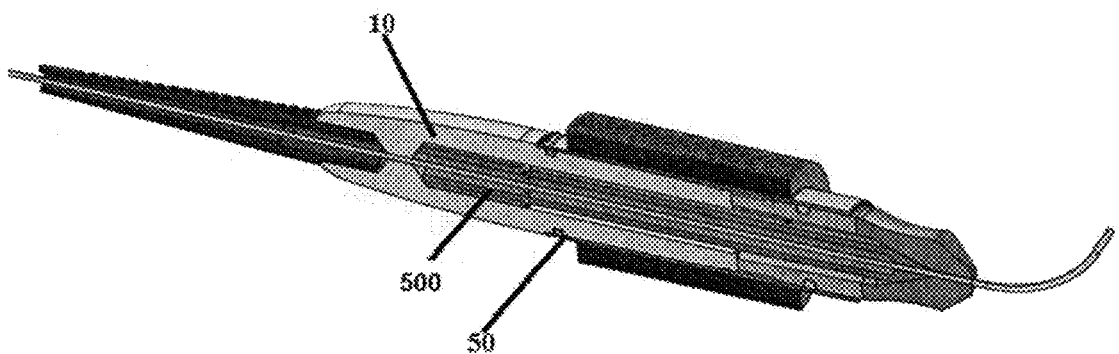

In yet further exemplary implementation, as illustrated in FIGS. 6 and 7, when reusable hand piece 10 and cover 50 are assembled, the cover 50 and hand piece 10 automatically line up such that the proximal (reusable) portion of probe 20 enters the cannula 70 until it hits the clear window 90. In an exemplary implementation a shield or cover 500, which may be optionally spring loaded, can be configured to cover components 410 of probe 20 and/or probe 20, and to retract, due to engagement with end wall 63, for example into body 12 as probe 20 advances into cannula 70 to prevent damage to components 410. In yet another exemplary implementation an index of refraction matched material can be provided in the end of the cannula 70 so there is no air gap between the proximal lenses and the distal clear window. In still further exemplary implementation, the above-described features can be applied in bent products as the reusable fibers, such as image, illumination and laser guides extending into the cannula 70 of the cover are flexible and can conform to the hollow bent cannula, as illustrated in the example of FIGS. 6 and 7. Of course, cannula 70 can also be straight, or not bent.

While the present disclosure has been shown and described with reference to certain exemplary embodiments thereof, it will be understood by those skilled in the art that various changes in form and details may be made therein without departing from the spirit and scope of the embodiments of the present disclosure. Furthermore, any of the features or elements of any exemplary implementations of the embodiments of the present disclosure as describes above and illustrated in the drawing figures can be implemented individually or in any combination(s) as would be readily appreciated by skilled artisans without departing from the spirit and scope of the embodiments of the present disclosure.

In addition, the included drawing figures further describe non-limiting examples of implementations of certain exemplary embodiments of the present disclosure and aid in the description of technology associated therewith. Any specific or relative dimensions or measurements provided in the drawings other as noted above are exemplary and not intended to limit the scope or content of the inventive design or methodology as understood by artisans skilled in the relevant field of disclosure.

Thus, the description and figures are intended by way of example only and are not intended to limit the illustrative embodiments in any way except as set forth in the appended claims and their full scope of equivalents. Also, various technical aspects of the various elements of the various exemplary embodiments that have been described above can be combined in numerous other ways, all of which are considered to be within the scope of the disclosure.

I claim:

1. A system comprising;
    a cover including
        a first body comprising a first cavity, and
        a hollow cannula in sealed communication with said first body and extending distally from said first cavity, said hollow cannula including a lumen open to said first cavity, said first body defining an end wall at a distal end of said first cavity, wherein said end wall radiates outwardly from an interface between said distal end of said first cavity and said hollow cannula, and
    a reusable endoscope including
        a hand piece having a second body,
        a probe extending distally from said second body, and
        a retractable shield covering at least a portion of said probe, said retractable shield having a distal end and a distally-facing end face located thereat,
    wherein said end wall is configured to engage with said end face of said retractable shield, upon an extent of distal movement of said retractable shield relative to said end wall, so as to restrict further distal movement of said retractable shield, and, wherein, upon said second body being inserted into said first cavity, said probe is inserted into said lumen of said hollow cannula to move distally relative to the retractable shield and extend distally beyond said distal end of said retractable shield, with said end face of said retractable shield being in engagement with said end wall.

2. The system of claim 1, wherein said second body comprises a second cavity and said retractable shield retracts proximally into said second cavity when said end face of said retractable shield engages said end wall.

3. The system of claim 1, wherein said retractable shield is biased distally from said second body toward a distal end of said probe.

4. The system of claim 1, wherein said cover is configured to snap-fit onto said endoscope when said second body is inserted into said cavity.

5. The system of claim 1, wherein said cover further comprises a sheath extendable proximally from said first body.

6. The system of claim 1, wherein said probe comprises an image guide, an illumination guide, and a laser guide.

7. The system of claim 1, wherein said cover further comprises an optically clear window at a distal end of said hollow cannula positioned to limit distal movement of said probe.

8. The system of claim 1, wherein said hollow cannula comprises an elongate body having at least one of a rigid portion, a flexible portion, a straight portion, and a curved portion.

\* \* \* \* \*